United States Patent
Niwa et al.

(10) Patent No.: US 9,359,328 B2
(45) Date of Patent: Jun. 7, 2016

(54) 2-[[[2-[(HYDROXYACETYL)AMINO]-4-PYRIDINYL]METHYL]THIO]-N-[4-(TRIFLUOROMETHOXY)PHENYL]-3-PYRIDINECARBOXAMIDE BENZENESULFONATE, CRYSTAL OF SAME, CRYSTAL POLYMORPH THEREOF, AND METHODS FOR PRODUCTION THEREOF

(71) Applicant: Santen Pharmaceutical Co., Ltd., Osaka-shi, Osaka (JP)

(72) Inventors: Masashi Niwa, Ikoma (JP); Hiroshi Deguchi, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/686,577

(22) Filed: Apr. 14, 2015

(65) Prior Publication Data
US 2015/0291560 A1 Oct. 15, 2015

Related U.S. Application Data

(62) Division of application No. 13/384,590, filed as application No. PCT/JP2010/062071 on Jul. 16, 2010, now Pat. No. 9,029,398.

(30) Foreign Application Priority Data

Jul. 17, 2009 (JP) ................................. 2009-169130

(51) Int. Cl.
C07D 213/82 (2006.01)
C07D 401/12 (2006.01)
A61K 31/455 (2006.01)

(52) U.S. Cl.
CPC ............ *C07D 401/12* (2013.01); *A61K 31/455* (2013.01); *C07D 213/82* (2013.01); *C07B 2200/13* (2013.01)

(58) Field of Classification Search
CPC .................................................. C07D 213/82
USPC ....................................................... 546/261
See application file for complete search history.

(56) References Cited

U.S. PATENT DOCUMENTS

| | | | |
|---|---|---|---|
| 7,544,703 B2 | 6/2009 | Honda et al. | |
| 2007/0149574 A1 | 6/2007 | Honda et al. | |
| 2009/0291951 A1 | 11/2009 | Tajima et al. | |

FOREIGN PATENT DOCUMENTS

| | | |
|---|---|---|
| CN | 1918127 | 2/2007 |
| EP | 1717229 | 11/2006 |
| EP | 1864977 | 12/2007 |
| JP | 2006-096739 A | 4/2006 |
| JP | 2006-306861 A | 11/2006 |

OTHER PUBLICATIONS

Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 183-226.*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Ivanisevic et al. "Use of X-ray . . . " Pharm. Sci. Encycl. p. 1-42 (2010).*
Seddon "Pseudopolymorph . . . " Crystal Growth & design v.4(6) p. 1087 (2004) (2 pages from internet).*
C.G. Wermuth, "The Practice of Medicinal Chemistry" ("Saishin Souyaku Kagaku, second volume"), Technomics, Inc., Sep. 25, 1999, pp. 359-365 and 452-453.
First Office Action Chinese Patent Application No. 201080031652.1 dated Apr. 19, 2013.
International Search Report in PCT/JP2010/062071 dated Aug. 10, 2010.
Japanese Office Action dated Jun. 24, 2014 issued in Application No. 2010-161881.
Lokesh Kumar et al., "Salt Selection in Drug Development", Pharmaceutical Technology Advanstar Communications, Inc. US, vol. 32, No. 3, Mar. 1, 2008, pp. 128-146.
Sadasuke Okano, "Shin—Yakuzaigaku Souron (revised 3rd Edition)" ("New—Outline of Pharmaceutics"), Nankodo, Inc., Apr. 10, 1987, pp. 26, 111 and 256-258.
Supplementary European Search Report EP Application No. 10799928.6 dated Dec. 7, 2012.

* cited by examiner

*Primary Examiner* — Patricia L Morris
(74) *Attorney, Agent, or Firm* — Foley & Lardner LLP

(57) ABSTRACT

In the course of developing 2-[[[2-[(hydroxyacetyl) amino]-4-pyridinyl]methyl]thio]-N-[4-(trifluoromethoxy) phenyl]-3-pyridinecarboxamide(compound A), there are the multiple problems: 1) compound A or its salt is difficult to be recrystallized, the storage stability largely differs depending on the kind of the salt, and it is very difficult to obtain a salt of compound A having excellent storage stability; 2) in a crystallization process of compound A, it is very difficult to control a crystal polymorph, and 3) compound A (free body) causes mineral deposition in the stomach when it is orally administered repeatedly. For solving these problems, we made examination focusing on the kind of the salt and, as a result, found that 1) benzenesulfonate of compound A does not decompose by light, humidity and other factors in a 1-week preliminary stability test (severe test), and has no problem in its storage stability, 2) a method of selectively producing two kinds of crystal forms of benzenesulfonate of compound A, and that 3) no mineral deposition in the stomach is observed even after a 4-week repeated oral administration.

2 Claims, No Drawings

US 9,359,328 B2

2-[[[2-[(HYDROXYACETYL)AMINO]-4-PYRIDINYL]METHYL]THIO]-N-[4-(TRIFLUOROMETHOXY)PHENYL]-3-PYRIDINECARBOXAMIDE BENZENESULFONATE, CRYSTAL OF SAME, CRYSTAL POLYMORPH THEREOF, AND METHODS FOR PRODUCTION THEREOF

CROSS-REFERENCE TO RELATED APPLICATIONS

The present application is a divisional of U.S. patent application Ser. No. 13/384,590, filed on Jul. 16, 2010, the entire disclosure of which is incorporated by reference herein.

TECHNICAL FIELD

The present invention relates to benzenesulfonate of 2-[[[2-[(hydroxyacetyl)amino]-4-pyridinyl]methyl]thio]-N-[4-(trifluoromethoxy)phenyl]-3-pyridinecarboxamide that is highly safe, excellent in storage stability, and useful as a pharmaceutical, a crystal of the same, a crystal polymorph thereof, and production methods thereof. The present invention also relates to a pharmaceutical containing at least one selected from the group consisting of benzenesulfonate of 2-[[[2-[(hydroxyacetyl) amino]-4-pyridinyl]methyl]thio]-N-[4-(trifluoromethoxy)phenyl]-3-pyridinecarboxamide, a crystal of the same, and a crystal polymorph thereof

BACKGROUND ART

Usually, for pharmaceutical products, safety, quality, and stable supply are required, as well as a therapeutic efficacy on diseases. Therefore, for a compound serving as an active ingredient of a pharmaceutical product, little side effect, excellent storage stability of the compound in various conditions (light, temperature, humidity and so on), and ease of process control in a production stage of the pharmaceutical product (ease of handling) and the like are requested, and the compound will be a pharmaceutical product only when all of these requirements are satisfied.

On the other hand, U.S. Patent Publication No. 2007/0149574 (PTL 1) describes that 2-[[[2-[(hydroxyacetyl)amino]-4-pyridinyl]methyl]thio]-N-[4-(trifluoromethoxy)phenyl]-3-pyridinecarboxamide exhibits a cell proliferation inhibiting effect in a test system using a VEGF-induced HUVEC proliferation reaction evaluation system, exhibits a tumor proliferation suppressing effect in a test system using a tumor-bearing mouse model, exhibits a paw edema suppressing effect in a test system using a rat adjuvant arthritis model, and exhibits a choroidal neovascularization inhibiting effect in a test system using a rat choroidal neovascularization model, and that, owing to these pharmacologic effects, 2-[[[2-[(hydroxyacetyl)amino]-4-pyridinyl]methyl]thio]-N-[4-(trifluoromethoxy)phenyl]-3-pyridinecarboxamide is useful as a pharmaceutical, and is especially expected as a prophylactic or therapeutic agent for diseases such as cancer, rheumatoid arthritis, age-related macular degeneration, diabetic retinopathy, diabetic macular edema and the like. PTL 1 also describes that 2-[[[2-[(hydroxyacetyl)amino]-4-pyridinyl]methyl]thio]-N-[4-(trifluoromethoxy)phenyl]-3-pyridinecarboxamide has a property of a light yellow solid.

However, PTL 1 lacks concrete description of benzenesulfonate of 2-[[[2-[(hydroxyacetyl)amino]-4-pyridinyl]methyl]thio]-N-[4-(trifluoromethoxy)phenyl]-3-pyridinecarboxamide, a crystal of the same, a crystal polymorph thereof and production methods thereof, and lacks description and suggestion of a problem that 2-[[[2-[(hydroxyacetyl)amino]-4-pyridinyl]methyl]thio]-N-[4-(trifluoromethoxy)phenyl]-3-pyridinecarboxamide will cause mineral deposition in the stomach when it is orally administered repeatedly.

CITATION LIST

Patent Literature

PTL 1: U.S. Patent Publication No. 2007/0149574

SUMMARY OF INVENTION

Technical Problem

In the course of developing 2-[[[2-[(hydroxyacetyl)amino]-4-pyridinyl]methyl]thio]-N-[4-(trifluoromethoxy)phenyl]-3-pyridinecarboxamide (hereinafter, also referred to as "compound A") that is useful as a pharmaceutical, the present inventors found that there were the following multiple problems: 1) compound A or its salt is difficult to be recrystallized, the storage stability largely differs depending on the kind of the salt, and it is very difficult to obtain a salt of compound A having excellent storage stability; 2) in a crystallization process of compound A or its salt, it is very difficult to control a crystal polymorph, and 3) compound A (free body) causes mineral deposition in the stomach when it is orally administered repeatedly.

Solution to Problem

In light of the above, the present inventors made diligent effort focusing on the kind of the salt in compound A for solving all of the aforementioned problems 1) to 3).

As a result, the present inventors found that compound A formed a salt with methanesulfonic acid, benzenesulfonic acid or p-toluenesulfonic acid. For examining the storage stability for these salts with compound A, a 1-week preliminary stability test (severe test) was executed. As a result, methanesulfonate of compound A decomposed by light, and p-toluenesulfonate decomposed by humidity, to cause a decrease in purity (decomposition) of about 1% to about 8%, demonstrating that these salts have great problems in storage stability. On the other hand, benzenesulfonate of compound A did not show a decrease in purity (decomposition) by light, humidity and other factors in a similar test, demonstrating that it has very high storage stability.

Focusing on the existence of a crystal polymorph of benzenesulfonate of compound A, the present inventors also found that benzenesulfonate of compound A has at least two crystal forms and found a method of producing the two crystal forms selectively.

Further, the present inventors found that mineral deposition in the stomach was observed in a rat 1-week repeated oral administration toxicity test (30 mg/kg) of compound A, whereas mineral deposition in the stomach was not observed in a rat 4-week repeated oral administration toxicity test (30 mg/kg) of benzenesulfonate of compound A, and accomplished the present invention. That is, the present invention is as follows.

The present invention is benzenesulfonate of 2-[[[2-[(hydroxyacetyl)amino]-4-pyridinyl]methyl]thio]-N-[4-(trifluoromethoxy)phenyl]-3-pyridinecarboxamide.

The present invention also provides a method of producing benzenesulfonate of 2-[[[2-[(hydroxyacetyl)amino]-4-pyridinyl]methyl]thio]-N-[4-(trifluoromethoxy)phenyl]-3-pyridinecarboxamide, including the step of adding 2-[[[2-[(hydroxyacetyl)amino]-4-pyridinyl]methyl]thio]-N-[4-

(trifluoromethoxy)phenyl]-3-pyridinecarboxamide to an organic solvent solution containing benzenesulfonic acid.

The present invention also provides a method of producing benzenesulfonate of 2-[[[2-[(hydroxyacetyl)amino]-4-pyridinyl]methyl]thio]-N-[4-(trifluoromethoxy)phenyl]-3-pyridinecarboxamide, including the step of adding at least either of benzenesulfonic acid and its hydrate to an organic solvent solution containing 2-[[[2-[(hydroxyacetyl)amino]-4-pyridinyl]methyl]thio]-N-[4-(trifluoromethoxy)phenyl]-3-pyridinecarboxamide.

Here, the organic solvent is preferably a non-protonic polar solvent or cyclic ether. Further, as the non-protonic polar solvent, dimethylsulfoxide or N,N-dimethylformamide is more preferred, and as the cyclic ether, tetrahydrofuran is more preferred.

The present invention is a crystal of benzenesulfonate of 2-[[[2-[(hydroxyacetyl)amino]-4-pyridinyl]methyl]thio]-N-[4-(trifluoromethoxy)phenyl]-3-pyridinecarboxamide.

The present invention also provides a so-called α-form crystal of benzenesulfonate of 2-[[[2-[(hydroxyacetyl)amino]-4-pyridinyl]methyl]thio]-N-[4-(trifluoromethoxy)phenyl]-3-pyridinecarboxamide having characteristic peaks at 4.4 angstroms, 3.8 angstroms and 2.3 angstroms as a d value of powder X-ray diffraction pattern.

The present invention also provides a method of producing a so-called α-form crystal of benzenesulfonate of 2-[[[2-[(hydroxyacetyl)amino]-4-pyridinyl]methyl]thio]-N-[4-(trifluoromethoxy)phenyl]-3-pyridinecarboxamide, including the steps of: adding 2-[[[2-[(hydroxyacetyl)amino]-4-pyridinyl]methyl]thio]-N-[4-(trifluoromethoxy)phenyl]-3-pyridinecarboxamide to a good solvent solution containing benzenesulfonic acid; and sequentially adding a poor solvent to the reaction solution.

The present invention also provides a method of producing a so-called α-form crystal of benzenesulfonate of 2-[[[2-[(hydroxyacetyl)amino]-4-pyridinyl]methyl]thio]-N-[4-(trifluoromethoxy)phenyl]-3-pyridinecarboxamide, including the steps of: adding at least either of benzenesulfonic acid and its hydrate to a good solvent solution containing 2-[[[2-[(hydroxyacetyl)amino]-4-pyridinyl]methyl]thio]-N-[4-(trifluoromethoxy)phenyl]-3-pyridinecarboxamide; and sequentially adding a poor solvent to the reaction solution.

Here, the good solvent is preferably a non-protonic polar solvent, and more preferably dimethylsulfoxide or N,N-dimethylformamide.

Here, the poor solvent is preferably a solvent that substantially fails to dissolve benzenesulfonate of 2-[[[2-[(hydroxyacetyl)amino]-4-pyridinyl]methyl]thio]-N-[4-(trifluoromethoxy)phenyl]-3-pyridinecarboxamide at room temperature, and is more preferably water, a lower alkyl alcohol, a lower alkyl ketone or a lower alkyl carboxylic acid ester, and the solvent is further preferably water, ethanol, acetone or ethyl acetate, and particularly preferably ethanol.

The present invention also provides a method of producing a so-called α-form crystal of benzenesulfonate of 2-[[[2-[(hydroxyacetyl)amino]-4-pyridinyl]methyl]thio]-N-[4-(trifluoromethoxy)phenyl]-3-pyridinecarboxamide, including the step of adding a poor solvent to a good solvent solution containing benzenesulfonate of 2-[[[2-[(hydroxyacetyl)amino]-4-pyridinyl]methyl]thio]-N-[4-(trifluoromethoxy)phenyl]-3-pyridinecarboxamide.

Here, the good solvent is preferably a non-protonic polar solvent, and more preferably dimethylsulfoxide or N,N-dimethylformamide.

Here, the poor solvent is preferably a solvent that substantially fails to dissolve benzenesulfonate of 2-[[[2-[(hydroxyacetyl)amino]-4-pyridinyl]methyl]thio]-N-[4-(trifluoromethoxy)phenyl]-3-pyridinecarboxamide at room temperature, and is more preferably water, a lower alkyl alcohol, a lower alkyl ketone or a lower alkyl carboxylic acid ester, and the solvent is particularly preferably water, ethanol, acetone or ethyl acetate.

The present invention also provides a method of producing a so-called α-form crystal of benzenesulfonate of 2-[[[2-[(hydroxyacetyl)amino]-4-pyridinyl]methyl]thio]-N-[4-(trifluoromethoxy)phenyl]-3-pyridinecarboxamide, including the steps of: adding and dissolving benzenesulfonate of 2-[[[2-[(hydroxyacetyl)amino]-4-pyridinyl]methyl]thio]-N-[4-(trifluoromethoxy)phenyl]-3-pyridinecarboxamide in a warmed lower alcohol; and sequentially cooling the lower alcohol solution.

Here, the lower alcohol is preferably methanol or ethanol.

The present invention also provides a so-called β-form crystal of benzenesulfonate of 2-[[[2-[(hydroxyacetyl)amino]-4-pyridinyl]methyl]thio]-N-[4-(trifluoromethoxy)phenyl]-3-pyridinecarboxamide having characteristic peaks at 8.1 angstroms, 6.8 angstroms, 4.1 angstroms and 4.0 angstroms as a d value of powder X-ray diffraction pattern.

The present invention also provides a method of producing a so-called β-form crystal of benzenesulfonate of 2-[[[2-[(hydroxyacetyl)amino]-4-pyridinyl]methyl]thio]-N-[4-(trifluoromethoxy)phenyl]-3-pyridinecarboxamide, including the step of adding 2-[[[2-[(hydroxyacetyl)amino]-4-pyridinyl]methyl]thio]-N-[4-(trifluoromethoxy)phenyl]-3-pyridinecarboxamide to a cyclic ether solution containing benzenesulfonic acid.

The present invention also provides a method of producing a so-called β-form crystal of benzenesulfonate of 2-[[[2-[(hydroxyacetyl)amino]-4-pyridinyl]methyl]thio]-N-[4-(trifluoromethoxy)phenyl]-3-pyridinecarboxamide, including the step of adding at least either of benzenesulfonic acid and its hydrate to a cyclic ether solution containing 2-[[[2-[(hydroxyacetyl)amino]-4-pyridinyl]methyl]thio]-N-[4-(trifluoromethoxy)phenyl]-3-pyridinecarboxamide.

Here, the cyclic ether is preferably tetrahydrofuran.

The present invention also provides a pharmaceutical containing as an active ingredient, at least one selected from the group consisting of any of the aforementioned benzenesulfonates, a crystal of the same, and a so-called α-form crystal and a so-called β-form crystal thereof The present invention also provides an oral or parenteral agent containing as an active ingredient, at least one selected from the group consisting of any of the aforementioned benzenesulfonates, a crystal of the same, and a so-called α-form crystal and a so-called β-form crystal thereof.

Advantageous Effects of Invention

The present invention provides benzenesulfonate of compound A that is highly safe, excellent in storage stability, and useful as a pharmaceutical, a crystal of the same, a crystal polymorph thereof, and production methods thereof The present invention also provides a pharmaceutical containing at least one selected from the group consisting of benzenesulfonate of compound A, a crystal of the same, and a crystal polymorph thereof

DESCRIPTION OF EMBODIMENTS

In the present invention, "2-[[[2-[(hydroxyacetyl)amino]-4-pyridinyl]methyl]thio]-N-[4-(trifluoromethoxy)phenyl]-3-pyridinecarboxamide" (compound A) means a compound represented by the following chemical structure formula (1).

[Chemical 1]

(1)

Compound A can be produced according to, but not limited to, the production method described in U.S. Patent Application Publication No. 2007/0149574 specification.

In the present invention, "benzenesulfonate of compound A" means a compound formed by the above chemical structure formula (1) and benzenesulfonic acid. A constituting ratio between compound A and benzenesulfonic acid is preferably 1:1 or 1:2, and is particularly preferably 1:1. Further, when the constituting ratio between compound A and benzenesulfonic acid is 1:1, "benzenesulfonate of compound A" is desirably a compound represented by the following chemical structural formula (2).

[Chemical 2]

(2)

(1) Production Method of Benzenesulfonate of Compound A

Benzenesulfonate of compound A can be produced by:

(1a) adding compound A to an organic solvent solution containing benzenesulfonic acid, or (1b) adding at least either of benzenesulfonic acid and its hydrate to an organic solvent solution containing compound A.

While the temperature at the time of executing (1a) or (1b) is not particularly limited insofar as salt formation progresses, it is executed preferably under ice cooling or at room temperature, and more preferably at 15 to 30° C.

The time of executing (1a) or (1b) is not particularly limited insofar as it is enough to allow progression of salt formation.

Further, benzenesulfonate of compound A generated in this operation can be isolated and/or purified by a widely used treatment method and/or purification method, for example, by using techniques such as concentration under reduced pressure, crystallization in water, an organic solvent and the like, filtration, washing, drying under reduced pressure and so on.

As the "organic solvent" in (1a) or (1b), any organic solvent capable of dissolving compound A may be used without any limitation, however, a non-protonic polar solvent or cycle ether is preferred.

As the "non-protonic polar solvent", any polar solvent not having a proton-donating ability may be used without any limitation, and for example, dimethylsulfoxide, N,N-dimethylformamide, N,N-dimethylacetamide, N-methylpyrrolidone, hexamethylphosphoramide and the like can be recited. Among these, dimethylsulfoxide or N,N-dimethylformamide is particularly preferred.

As the "cyclic ether", any cyclic ether containing 1 to 6 carbon atom(s) and one or two oxygen atom(s) may be used without any limitation, and for example, oxirane, oxetane, tetrahydrofuran, tetrahydropyran, [1,4]dioxane, oxepane, oxocane and the like are recited. Among these, tetrahydrofuran is particularly preferred.

(2) Production Method of So-Called α-Form Crystal of Benzenesulfonate of Compound A A so-called α-form crystal of benzenesulfonate of compound A can be produced by:

(2a) adding compound A to a good solvent solution containing benzenesulfonic acid, followed by adding a poor solvent to the reaction solution, or (2b) adding at least either of benzenesulfonic acid and its hydrate to a good solvent solution containing compound A, followed by adding a poor solvent to the reaction solution, or (2c) adding a poor solvent to a good solvent solution containing benzenesulfonate of compound A, or (2d) adding and dissolving benzenesulfonate of compound A in a warmed lower alcohol, followed by cooling the lower alcohol solution.

While the temperature at the time of executing (2a) or (2b) is not particularly limited insofar as salt formation progresses, it is executed preferably under ice cooling or at room temperature, and more preferably at 15 to 30° C.

While the temperature during and after the addition of the poor solvent in executing (2a), (2b) or (2c) is not particularly limited insofar as crystallization progresses, it is executed preferably at room temperature, and more preferably at 15 to 30° C.

While the warming in executing (2d) is not particularly limited insofar as it is such a degree of warming that allows (complete) dissolution of benzenesulfonate of compound A in a lower alcohol, the warming temperature is preferably 40 to 70° C., and more preferably 45 to 65° C.

While the cooling after the warming may be conducted at any temperature without any limitation insofar as crystallization progresses, it is preferably executed under ice cooling or at room temperature (allowing to cool), and more preferably at 15 to 30° C.

The reaction time in executing (2a) or (2b) is not particularly limited insofar as it is enough for the reaction to progress.

While the crystallization time after the addition of the poor solvent in executing (2a), (2b), (2c) or (2d) is not particularly limited insofar as crystallization progresses, it is executed preferably for 0.25 hours to 48 hours, and more preferably 3 hours to 24 hours.

Further, a so-called α-form crystal of benzenesulfonate of compound A generated in the reaction or the like can be isolated and/or purified by a widely used treatment method and/or purification method, for example, by using techniques such as concentration under reduced pressure, crystallization in water, an organic solvent and the like, filtration, washing, drying under reduced pressure and so on.

The "good solvent" in (2a), (2b) or (2c) means "an organic solvent capable of dissolving benzenesulfonate of compound A", and preferably, a non-protonic polar solvent is recited, and particularly preferably, dimethylsulfoxide or N,N-dimethylformamide is recited.

Here, the "non-protonic polar solvent" is not particularly limited insofar as it is a polar solvent not having a proton donating ability, and for example, dimethylsulfoxide, N,N-dimethylformamide, N,N-dimethylacetamide, N-methylpyrrolidone or hexamethylphosphoramide is recited, and among these, dimethylsulfoxide or N,N-dimethylformamide is preferred.

The "poor solvent" means a "solvent substantially not dissolving benzenesulfonate of compound A at room temperature", and for example, water, a lower alcohol, a lower alkyl ketone or a lower alkyl carboxylic acid ester is recited, and among these, a lower alcohol is preferred.

Here, the "lower alcohol" means an alcohol having 1 to 6 carbon atom(s), and for example, methanol, ethanol, propanol, isopropanol, butanol, isobutanol or tert-butanol is recited, and among these methanol or ethanol is preferred.

The "lower alkyl ketone" means an alkyl ketone having 1 to 13, preferably 1 to 7 carbon atom(s), and for example, acetone, methylethylketone or diethylketone is recited, and among these acetone is preferred. The "lower alkyl carboxylic acid ester" means an alkyl carboxylic acid ester having 1 to 13, preferably 1 to 7 carbon atom(s), and for example, ethyl acetate, methyl acetate or isopropyl acetate is recited, and among these ethyl acetate is preferred.

As to the ratio between the "good solvent" and the "poor solvent", the ratio of the good solvent and the poor solvent may be appropriately selected within the range of 10:1 to 1:10 depending on the kinds of the good solvent and the poor solvent. For example, when the good solvent is dimethylsulfoxide and the poor solvent is water, the ratio of these is preferably in the range of 3:1 to 1:1, and more preferably in the range of 2:1. When the good solvent is dimethylsulfoxide and the poor solvent is ethanol, the ratio of these is preferably in the range of 1:3 to 1:7, more preferably in the range of 1:4 to 1:6, and particularly preferably 1:5. When the good solvent is dimethylsulfoxide and the poor solvent is acetone, the ratio of these is preferably in the range of 1:3 to 1:7, more preferably in the range of 1:4 to 1:6, and particularly preferably 1:5. When the good solvent is dimethylsulfoxide and the poor solvent is ethyl acetate, the ratio of these is preferably in the range of 1:2 to 1:6, more preferably in the range of 1:3 to 1:5, and particularly preferably 1:4.

In (2d), the "lower alcohol" means an alcohol having 1 to 6 carbon atom(s), and for example, methanol, ethanol, propanol, isopropanol, butanol, isobutanol or tert-butanol is recited, and among these methanol or ethanol is preferred. (3) Production method of a so-called β-form crystal of benzenesulfonate of compound A A so-called β-form crystal of benzenesulfonate of compound A can be produced by:

(3a) adding compound A to a cyclic ether solution containing benzenesulfonic acid, or (3b) adding at least either of benzenesulfonic acid and its hydrate to a cyclic ether solution containing compound A.

While the temperature at the time of executing (3a) or (3b) is not particularly limited insofar as salt formation progresses, it is executed preferably under ice cooling or at room temperature, and more preferably at 15 to 30° C.

The reaction time in executing (3a) or (3b) is not particularly limited insofar as it is enough for the reaction to progress.

Further, a so-called β-form crystal of benzenesulfonate of compound A generated in the reaction or the like can be isolated and/or purified by a widely used treatment method and/or purification method, for example, by using techniques such as concentration under reduced pressure, crystallization in water, an organic solvent and the like, filtration, washing, drying under reduced pressure and so on.

The "cyclic ether" in (3a) or (3b) is not particularly limited insofar as it is a cyclic ether capable of dissolving compound A and being a poor solvent with respect to benzenesulfonate of compound A, and cyclic ethers containing 2 to 6 carbon atom(s) and one or two oxygen atom(s) are recited. Preferably, oxirane, oxetane, tetrahydrofuran, tetrahydropyran, [1,4]dioxane, oxepane, oxocane or the like are recited, and particularly preferably, tetrahydrofuran is recited.

While two forms of crystals called an α-form and a β-form exist as crystals of benzenesulfonate of compound A, crystal polymorphs other than these, if exist, are also involved in crystals of benzenesulfonate of compound A of the present invention.

In the following, benzenesulfonate of compound A, a crystal of the same and a crystal polymorph thereof (including a so-called α-form crystal and a so-called β-form crystal) are also referred to as a "present compound".

While the present compound can absorb water and have adsorbed water, or become a hydrate when it is left still in atmospheric air or recrystallized, such a hydrate is also involved in the present invention.

Since the present compound exhibits a cell proliferation inhibiting effect in a test system using a VEGF-induced HUVEC proliferation reaction evaluation system, exhibits a tumor proliferation suppressing effect in a test system using a tumor-bearing mouse model, exhibits a paw edema suppressing effect in a test system using a rat adjuvant arthritis model, and exhibits a choroidal neovascularization inhibiting effect in a test system using a rat choroidal neovascularization model, it is useful as a pharmaceutical, and is especially useful as a prophylactic or therapeutic agent for diseases such as cancer, rheumatoid arthritis, age-related macular degeneration, diabetic retinopathy, diabetic macular edema and the like. The pharmaceutical is for use in a warm-blooded animal, and preferably for a human being.

When the present compound is used as a prophylactic or therapeutic drug for the aforementioned diseases, the present compound can be administered either orally or parenterally. As a dosage form, tablet, capsule, granule and powder are recited as oral agents, and injection, eye drop, nasal drop, transdermally absorbable agent, aerosol (including "inhalant") and the like are recited as parenteral agents, and they may be formulated using widely used techniques.

For example, oral agents such as tablet, capsule, granule and powder can be prepared while using excipients such as lactose, mannitol, starch, crystalline cellulose, light anhydrous silicic acid, calcium carbonate and calcium hydrogen phosphate, lubricants such as stearic acid, magnesium stearate and talc, binders such as starch, hydroxypropyl cellulose, hypromellose and polyvinyl pyrrolidone, disintegrants such as carboxymethyl cellulose, low substitution degree hydroxypropyl cellulose and calcium citrate, coating agents such as hypromellose, hydroxymethyl cellulose, macrogol and silicone resin, stabilizers such as ethyl paraoxybenzoate and benzyl alcohol, flavoring agents such as sweetener, acidulant and flavor, and the like as necessary.

Further, parenteral agents such as injection and eye drop can be prepared while using isotonizing agents such as sodium chloride, concentrated glycerin, propylene glycol, polyethylene glycol, potassium chloride, sorbitol and mannitol, buffering agents such as sodium phosphate, sodium hydrogen phosphate, sodium acetate, citric acid, glacial acetic acid and trometamol, surfactants such as polyoxyethylene sorbitan monooleate, polyoxyl 40 stearate and polyoxyethylene hydrogenated castor oil, stabilizing agents such as sodium citrate and sodium edetate, preservatives such as benzalkonium chloride, paraben, benzethonium chloride, paraoxybenzoic acid ester, sodium benzoate and chlorobutanol, pH modifiers such as hydrochloric acid, citric acid, phosphoric acid, glacial acetic acid, sodium hydroxide, sodium carbonate and sodium hydrogen carbonate, soothing agents such as benzyl alcohol, thickening agents such as hypromellose, and the like as necessary.

A dosage of the present compound can be appropriately selected and used according to the symptom, age, dosage form and the like. For example, an oral agent may be typically administered in a dosage of 0.01 to 1000 mg, preferably 1 to 100 mg per day by a single dose or in several doses. An eye drop can be typically administered in a concentration of 0.0001 to 10% (w/v), preferably 0.01 to 5% (w/v) by a single dose or in several doses.

Hereinafter, production examples of the present compound, a storage stability test and a result of the same, a side effect verification test and a result of the same, and formulation examples will be described, however, it is to be noted that these examples are given for better understanding of the present invention and not for limiting the scope of the present invention. Hereinafter, "$^1$H-NMR" means "proton nuclear magnetic resonance", "PXRD" means "powder X-ray diffraction", "DSC" means "differential scanning calorimeter measurement", "TGA" means "thermogravimetric apparatus", and "RH" means "relative humidity".

PRODUCTION EXAMPLES

Example 1

Production Method of Benzenesulfonate of Compound A

To compound A (200 mg) was added tetrahydrofuran (2 mL) and stirred at room temperature. After confirming dissolution, benzenesulfonic acid monohydrate (85 mg) was added at the same temperature. After end of salt formation, the solvent was distilled off under reduced pressure. To the concentrated residue was added ethyl acetate, and the precipitated solid was collected by filtration, and dried under reduced pressure to obtain benzenesulfonate of compound A in white (171 mg).

$^1$H-NMR (500 MHz, DMSO-$d_6$)
δ 4.02 (s,2H), 4.44 (s,2H), 7.17 (dd,J=4.9,1.5 Hz,1H), 7.28-7.38 (m,5H), 7.58-7.60 (m,2H), 7.71 (d,J=1.2 Hz,1H), 7.80-7.82 (m,2H), 7.99 (dd,J=7.6,1.8 Hz,1H), 8.20 (d,J=5.2 Hz,2H), 8.60 (dd,J=4.9,1.8 Hz,1H), 10.66 (s,1H)

Example 2

Production Method 1 of Benzenesulfonate of Compound A (α Crystal) (Ethyl Acetate/DMSO)

To compound A (503 mg) was added dimethylsulfoxide (2.0 mL) and stirred at room temperature. After confirming dissolution, benzenesulfonic acid monohydrate (207 mg) was added at the same temperature, and stirred for another 1.25 hours. Sequentially, ethyl acetate (15 mL) was added, and stirred for another 3.5 hours. The precipitated solid was collected by filtration, and dried under reduced pressure, to obtain benzenesulfonate of compound A in white (510 mg).

$^1$H-NMR (500 MHz, DMSO-$d_6$):
δ 4.05 (s,2H), 4.47 (s,2H), 7.28-7.38 (m,7H), 7.58-7.60 (m,2H), 7.81 (d,J=9.2 Hz,2H), 8.01 (dd,J=7.6,1.8 Hz,1H), 8.16 (s,1H), 8.24 (d,J=5.5 Hz,1H), 8.59 (dd,J=4.9,1.5 Hz,1H), 10.08 (bs,1H), 10.66 (s,1H)
PXRD:

TABLE 1

| Peak Angstrom | Angle 2θ° |
|---|---|
| d = 4.4627 | 19.878 |
| d = 4.3709 | 20.300 |
| d = 3.8408 | 23.139 |
| d = 2.3377 | 38.477 |

TGA:
Endothermic peak: 206.2° C.

Example 3

Production Method 2 of Benzenesulfonate of Compound A (α Crystal) (Ethanol/DMSO)

To compound A (505 mg) was added dimethylsulfoxide (2.0 mL) and stirred at room temperature. After confirming dissolution, benzenesulfonic acid monohydrate (200 mg) was added at the same temperature, and stirred for another 1.25 hours. Sequentially, ethanol (10 mL) was added, and stirred for another 2.5 hours. The precipitated solid was collected by filtration, and dried under reduced pressure, to obtain benzenesulfonate of compound A in white (482 mg).

$^1$H-NMR (500 MHz, DMSO-$d_6$):
δ 4.07 (s,2H), 4.49 (s,2H), 7.29-7.39 (m,7H), 7.58-7.60 (m,2H), 7.81 (d,J=9.2 Hz,2H), 8.03 (dd,J=7.6,1.8 Hz,1H), 8.15 (s,1H), 8.27 (d,J=5.5 Hz,1H), 8.59 (dd,J=4.9,1.8 Hz,1H), 10.32 (bs,1H), 10.67 (s,1H)
PXRD:

TABLE 2

| Peak Angstrom | Angle 2θ° |
|---|---|
| d = 4.4670 | 19.859 |
| d = 4.3711 | 20.300 |
| d = 3.8438 | 23.120 |
| d = 2.3377 | 38.478 |

TGA:
Endothermic peak: 207.7° C.

Example 4

Production Method 3 of Benzenesulfonate of Compound A (α Crystal) (Ethanol/DMSO)

To benzenesulfonic acid monohydrate (388 g) was added dimethylsulfoxide (1650 g) at room temperature (internal temperature 28° C.). Sequentially, compound A (750 g) was added at the same temperature. After stirring for 2.0 hours at room temperature, the solution was filtered. Sequentially, to the filtrate was added ethanol (5938 g) and stirred for 2.0 hours at room temperature. The precipitated solid was collected by filtration, and dried under reduced pressure, to obtain benzenesulfonate of compound A in white (820 g).

¹H-NMR (500 MHz,DMSO-d₆):

δ 4.08 (s,2H), 4.49 (s,2H), 7.29-7.39 (m,7H), 7.58-7.61 (m,2H), 7.81 (d,J=9.2 Hz,2H), 8.03 (dd,J=7.8,1.8 Hz,1H), 8.14 (s,1H), 8.27 (d,J=5.5 Hz,1H), 8.59 (dd,J=5.0,1.8 Hz,1H), 10.40 (bs,1H), 10.66 (s,1H)

PXRD:

TABLE 3

| Peak Angstrom | Angle 2θ° |
|---|---|
| d = 4.4579 | 19.900 |
| d = 4.3624 | 20.340 |
| d = 3.8405 | 23.141 |
| d = 2.3364 | 38.500 |

Example 5

Production Method 4 of Benzenesulfonate of Compound A (α Crystal) (Methanol, Leaving Still at Room Temperature)

To benzenesulfonate of compound A (99 mg) was added methanol (3 mL), and then stirred at an external temperature of 65° C. for 4 minutes. After confirming dissolution, the reaction was left still overnight at room temperature. The precipitated solid was collected by filtration, and dried under reduced pressure, to obtain benzenesulfonate of compound A in white (50 mg).

¹H-NMR (500 MHz,DMSO-d₆)

δ 4.12 (s,2H), 4.52 (s,2H), 7.30 (dd,J=4.6,1.5 Hz,1H), 7.31-7.34 (m,4H), 7.38 (d,J=8.6 Hz,2H), 7.47 (d,J=5.8 Hz,1H), 7.60-7.62 (m,2H), 7.81-7.83 (m,2H), 8.05 (dd,J=7.6, 1.5 Hz,1H), 8.12 (s,1H), 10.68 (s,1H), 10.83 (s,1H)

Example 6

Production Method 5 of Benzenesulfonate of Compound A (α Crystal) (Ethanol, Leaving Still at Room Temperature)

To benzenesulfonate of compound A (99 mg) was added ethanol (5 mL), and then stirred at an external temperature of 85° C. for 3 minutes. After confirming dissolution, the reaction was left still overnight at room temperature. The precipitated solid was collected by filtration, and dried under reduced pressure, to obtain benzenesulfonate of compound A in white (66 mg).

¹H-NMR (500 MHz,DMSO-d₆)

δ 4.11 (s,2H), 4.52 (s,2H), 7.30 (dd,J=4.6,2.4 Hz,1H), 7.31-7.34 (m,4H), 7.38 (d,J=8.6 Hz,2H), 7.44 (s,1H), 7.60-7.61 (m,2H), 7.81-7.83 (m,2H), 8.05 (d,J=7.6 Hz,1H), 8.12 (s,1H), 10.67 (s,1H), 10.83 (bs,1H)

Example 7

Production Method 6 of Benzenesulfonate of Compound A (α Crystal) (Ethyl Acetate/DMSO, Leaving Still at Room Temperature)

To benzenesulfonate of compound A (1.0 g) was added dimethylsulfoxide (1.5 mL), and then stirred at an internal temperature of 50° C. for 11 minutes. After confirming dissolution, ethyl acetate (6.0 mL) was added. After leaving still overnight at room temperature, the precipitated solid was collected by filtration, and dried under reduced pressure, to obtain benzenesulfonate of compound A in white (619 mg).

¹H-NMR (500 MHz,DMSO-d₆):

δ 4.07 (s,2H), 4.49 (s,2H), 7.29-7.39 (m,7H), 7.59-7.61 (m,2H), 7.81 (d,J=9.2 Hz,2H), 8.03 (d,J=7.6 Hz,1H), 8.14 (s,1H), 8.26 (d,J=5.5 Hz,1H), 8.58 (dd,J=4.9,1.8 Hz,1H), 10.35 (bs,1H), 10.66 (s,1H)

PXRD:

TABLE 4

| Peak Angstrom | Angle 2θ° |
|---|---|
| d = 4.4665 | 19.861 |
| d = 4.3670 | 20.319 |
| d = 3.8408 | 23.138 |
| d = 2.3399 | 38.440 |

TGA:

Endothermic peak: 207.2° C.

Example 8

Production Method 7 of Benzenesulfonate of Compound A (α Crystal) (Ethyl Acetate/DMSO, Leaving Still at Room Temperature)

To benzenesulfonate of compound A (1.0 g) was added dimethylsulfoxide (1.5 mL), and then stirred at an internal temperature of 50° C. for 6 minutes. After confirming dissolution, ethyl acetate (6.0 mL) was added. After stirring for 4.5 hours at room temperature, the precipitated solid was collected by filtration, and dried under reduced pressure, to obtain benzenesulfonate of compound A in white (701 mg).

¹H-NMR(500 MHz,DMSO-d₆):

δ 4.08 (s,2H), 4.49 (s,2H), 7.29-7.39 (m,7H), 7.59-7.61 (m,2H), 7.81 (d,J=9.2 Hz,2H), 8.03 (d,J=7.6 Hz,1H), 8.14 (s,1H), 8.27 (d,J=5.8 Hz,1H), 8.59 (dd,J=4.9,1.8 Hz,1H), 10.39 (bs,1H), 10.66 (s,1H)

PXRD:

TABLE 5

| Peak Angstrom | Angle 2θ° |
|---|---|
| d = 4.4627 | 19.879 |
| d = 4.3673 | 20.318 |
| d = 3.8437 | 23.121 |
| d = 2.3366 | 38.495 |

TGA:

Endothermic peak: 209.2° C.

Example 9

Production Method 8 of Benzenesulfonate of Compound A (α Crystal) (Ethyl Acetate/DMSO, Leaving Still Under Ice Cooling)

To benzenesulfonate of compound A (1.0 g) was added dimethylsulfoxide (1.5 mL), and then stirred at an internal temperature of 50° C. for 6 minutes. After confirming dissolution, ethyl acetate (6.0 mL) was added. After leaving still overnight under ice cooling (internal temperature 5° C.), the precipitated solid was collected by filtration, and dried under reduced pressure, to obtain benzenesulfonate of compound A in white (227 mg).

¹H-NMR (500 MHz,DMSO-d₆):

δ 4.08 (s,2H), 4.49 (s,2H), 7.30-7.39 (m,7H), 7.59-7.61 (m,2H), 7.81 (d,J=9.2 Hz,2H), 8.02 (d,J=6.4 Hz,1H), 8.14 (s,1H), 8.27 (d,J=5.5 Hz,1H), 8.59 (m,1H), 10.36 (bs,1H), 10.66 (s,1H)

PXRD:

TABLE 6

| Peak Angstrom | Angle 2θ° |
|---|---|
| d = 4.4670 | 19.859 |
| d = 4.3664 | 20.321 |
| d = 3.8409 | 23.138 |
| d = 2.3375 | 38.480 |

TGA:
Endothermic peak: 207.1° C.

Example 10

Production Method 9 of Benzenesulfonate of Compound A (α Crystal) (Acetone/DMSO, Stirring at Room Temperature)

To benzenesulfonate of compound A (1.0 g) was added dimethylsulfoxide (1.5 mL), and then stirred at an internal temperature of 50° C. for 5 minutes. After confirming dissolution, acetone (7.0 mL) was added. After stirring for 5.0 hours at room temperature, the precipitated solid was collected by filtration, and dried under reduced pressure, to obtain benzenesulfonate of compound A in white (629 mg).

¹H-NMR (500 MHz,DMSO-d₆):

δ 4.08 (s,2H), 4.49 (s,2H), 7.29-7.39 (m,7H), 7.59-7.61 (m,2H), 7.81 (d,J=9.2 Hz,2H), 8.03 (dd,J=7.6,1.8 Hz,1H), 8.14 (s,1H), 8.27 (d,J=5.8 Hz,1H), 8.59 (dd,J=4.9,1.8 Hz,1H), 10.39 (bs,1H), 10.66 (s,1H)

PXRD:

TABLE 7

| Peak Angstrom | Angle 2θ° |
|---|---|
| d = 4.4628 | 19.878 |
| d = 4.3746 | 20.283 |
| d = 3.8378 | 23.157 |
| d = 2.3376 | 38.480 |

Example 11

Production Method 10 of Benzenesulfonate of Compound A (α Crystal) (Acetone/DMSO, Leaving Still under Ice Cooling)

To benzenesulfonate of compound A (1.0 g) was added dimethylsulfoxide (1.5 mL), and then stirred at an internal temperature of 50° C. for 5 minutes. After confirming dissolution, acetone (7.0 mL) was added. After leaving still overnight under ice cooling (internal temperature 5° C.), the precipitated solid was collected by filtration, and dried under reduced pressure, to obtain benzenesulfonate of compound A in white (224 mg).

¹H-NMR (500 MHz,DMSO-d₆):

δ 4.08 (s,2H), 4.49 (s,2H), 7.29-7.39 (m,7H), 7.59-7.61 (m,2H), 7.81 (d,J=8.9 Hz,2H), 8.03 (dd,J=7.6,1.5 Hz,1H), 8.14 (s,1H), 8.27 (d,J=5.8 Hz,1H), 8.59 (dd,J=4.9,1.5 Hz,1H), 10.37 (bs,1H), 10.66 (s,1H)

PXRD:

TABLE 8

| Peak Angstrom | Angle 2θ° |
|---|---|
| d = 4.4712 | 19.840 |
| d = 4.3709 | 20.300 |
| d = 3.8472 | 23.100 |
| d = 2.3399 | 38.440 |

Example 12

Production Method 11 of Benzenesulfonate of Compound A (α Crystal) (Water/DMSO, Leaving Still at Room Temperature)

To benzenesulfonate of compound A (1.0 g) was added dimethylsulfoxide (1.5 mL), and then stirred at an internal temperature of 50° C. for 6 minutes. After confirming dissolution, water (0.8 mL) was added. After leaving still for 1 hour at room temperature, the precipitated solid was collected by filtration, and dried under reduced pressure, to obtain benzenesulfonate of compound A in white (928 mg).

¹H-NMR (500 MHz,DMSO-d₆):

δ 4.08 (s,2H), 4.49 (s,2H), 7.29-7.39 (m,7H), 7.59-7.61 (m,2H), 7.81 (d,J=9.2 Hz,2H), 8.03 (dd,J=7.6,1.5 Hz,1H), 8.14 (s,1H), 8.27 (d,J=5.8 Hz,1H), 8.59 (dd,J=4.9,1.8 Hz,1H), 10.36 (bs,1H), 10.66 (s,1H)

PXRD:

TABLE 9

| Peak Angstrom | Angle 2θ° |
|---|---|
| d = 4.4673 | 19.858 |
| d = 4.3710 | 20.300 |
| d = 3.8469 | 23.101 |
| d = 2.3376 | 38.479 |

TGA:
Endothermic peak: 205.5° C.

Example 13

Production Method 12 of Benzenesulfonate of Compound A (α Crystal) (Water/DMSO, Stirring at Room Temperature)

To benzenesulfonate of compound A (1.0 g) was added dimethylsulfoxide (1.5 mL), and then stirred at an internal temperature of 50° C. for 5 minutes. After confirming dissolution, water (0.8 mL) was added. After stirring for 0.5 hours at room temperature, the precipitated solid was collected by filtration, and dried under reduced pressure, to obtain benzenesulfonate of compound A in white (910 mg).

¹H-NMR (500 MHz,DMSO-d₆):

δ 4.08 (s,2H), 4.49 (s,2H), 7.29-7.39 (m,7H), 7.59-7.61 (m,2H), 7.81 (d,J=9.2 Hz,2H), 8.03 (dd,J=7.6,1.8 Hz,1H), 8.14 (s,1H), 8.27 (d,J=5.8 Hz,1H), 8.59 (dd,J=4.9,1.5 Hz,1H), 10.40 (bs,1H), 10.66 (s,1H)

PXRD:

TABLE 10

| Peak Angstrom | Angle 2θ° |
|---|---|
| d = 4.4662 | 19.863 |
| d = 4.3672 | 20.318 |
| d = 3.8439 | 23.120 |
| d = 2.3376 | 38.479 |

Example 14

Production Method 13 of Benzenesulfonate of Compound A (α Crystal) (Water/DMSO, Leaving Still Under Ice Cooling)

To benzenesulfonate of compound A (1.0 g) was added dimethylsulfoxide (1.5 mL), and then stirred at an internal temperature of 50° C. for 5 minutes. After confirming dissolution, water (0.8 mL) was added. After leaving still overnight under ice cooling (internal temperature 7° C.), the precipitated solid was collected by filtration, and dried under reduced pressure, to obtain benzenesulfonate of compound A in white (927 mg).

$^1$H-NMR (500 MHz,DMSO-d$_6$):

δ 4.08 (s,2H), 4.49 (s,2H), 7.29-7.39 (m,7H), 7.59-7.61 (m,2H), 7.81 (d,J=8.9 Hz,2H), 8.03 (dd,J=7.6,1.5 Hz,1H), 8.14 (s,1H), 8.27 (d,J=5.5 Hz,1H), 8.59 (dd,J=4.9,1.5 Hz,1H), 10.41 (bs,1H), 10.66 (s,1H)

PXRD:

TABLE 11

| Peak Angstrom | Angle 2θ° |
|---|---|
| d = 4.4628 | 19.878 |
| d = 4.3710 | 20.300 |
| d = 3.8407 | 23.139 |
| d = 2.3366 | 38.496 |

Example 15

Production Method 14 of Benzenesulfonate of Compound A (α Crystal) (Ethanol/DMSO, Leaving Still at Room Temperature)

To benzenesulfonate of compound A (1.0 g) were added dimethylsulfoxide (2.7 mL) and ethanol (6.0 mL), and then stirred at an internal temperature of 50° C. for 5 minutes. After leaving still overnight at room temperature, the precipitated solid was collected by filtration, and dried under reduced pressure, to obtain benzenesulfonate of compound A in white (104 mg).

$^1$H-NMR (500 MHz,DMSO-d$_6$):

δ 4.08 (s,2H), 4.49 (s,2H), 7.29-7.39 (m,7H), 7.59-7.61 (m,2H), 7.81 (d,J=9.2 Hz,2H), 8.03 (dd,J=7.6,1.8 Hz,1H), 8.14 (s,1H), 8.27 (d,J=6.1 Hz,1H), 8.59 (dd,J=4.9,1.8 Hz,1H), 10.39 (bs,1H), 10.66 (s,1H)

TGA:

Endothermic peak: 210.1° C.

Example 16

Production Method 15 of Benzenesulfonate of Compound A (α Crystal) (Ethanol/DMSO, Stirring at Room Temperature)

To benzenesulfonate of compound A (1.0 g) was added dimethylsulfoxide (2.5 mL), and then stirred at an internal temperature of 50° C. for 5 minutes. After confirming dissolution, ethanol (3.0 mL) was added. After stirring at room temperature for 5.0 hours, the precipitated solid was collected by filtration, and dried under reduced pressure, to obtain benzenesulfonate of compound A in white (71 mg).

$^1$H-NMR (500 MHz,DMSO-d$_6$):

δ 4.08 (s,2H), 4.49 (s,2H), 7.29-7.39 (m,7H), 7.59-7.61 (m,2H), 7.81 (d,J=9.2 Hz,2H), 8.03 (dd,J=7.6,1.5 Hz,1H), 8.14 (s,1H), 8.27 (d,J=5.8 Hz,1H), 8.59 (dd,J=4.9,1.8 Hz,1H), 10.40 (bs,1H), 10.66 (s,1H)

TGA:

Endothermic peak: 210.7° C.

Example 17

Production Method 16 of Benzenesulfonate of Compound A (α crystal) (Ethanol/DMSO, Leaving Still Under Ice Cooling)

To benzenesulfonate of compound A (1.0 g) were added dimethylsulfoxide (3.3 mL) and ethanol (6.0 mL), and then stirred at an internal temperature of 50° C. for 15 minutes. After leaving still overnight under ice cooling (internal temperature 4° C.), the precipitated solid was collected by filtration, and dried under reduced pressure, to obtain benzenesulfonate of compound A in white (301 mg).

$^1$H-NMR (500 MHz,DMSO-d$_6$):

δ 4.08 (s,2H), 4.49 (s,2H), 7.29-7.39 (m,7H), 7.59-7.61 (m,2H), 7.81 (d,J=9.2 Hz,2H), 8.03 (d,J=7.6 Hz,1H), 8.14 (s,1H), 8.27 (d,J=5.5 Hz,1H), 8.59 (dd,J=4.9,1.8 Hz,1H), 10.37 (bs,1H), 10.66 (s,1H)

PXRD:

TABLE 12

| Peak Angstrom | Angle 2θ° |
|---|---|
| d = 4.4665 | 19.861 |
| d = 4.3709 | 20.301 |
| d = 3.8438 | 23.120 |
| d = 2.3398 | 38.441 |

Example 18

Production Method 17 of Benzenesulfonate of Compound A (α crystal) (Ethanol/DMSO, Leaving Still at Room Temperature)

To benzenesulfonate of compound A (4.0 g) was added dimethylsulfoxide (9.0 mL), and then stirred at room temperature (internal temperature 25° C.) for 6 minutes. After confirming dissolution, ethanol (45 mL) was added. After stirring at room temperature for 1.0 hour, the precipitated solid was collected by filtration, and dried under reduced pressure, to obtain benzenesulfonate of compound A in white (3.3 g).

¹H-NMR (500 MHz, DMSO-$d_6$):

δ 4.08 (s,2H), 4.49 (s,2H), 7.30-7.39 (m,7H), 7.59-7.61 (m,2H), 7.81 (d,J=9.2 Hz,2H), 8.03 (dd,J=7.6,1.5 Hz,1H), 8.14 (s,1H), 8.27 (d,J=5.8 Hz,1H), 8.59 (dd,J=4.9,1.5 Hz,1H), 10.40 (bs,1H), 10.67 (s,1H)

PXRD:

TABLE 13

| Peak Angstrom | Angle 2θ° |
| --- | --- |
| d = 4.4705 | 19.843 |
| d = 4.3709 | 20.300 |
| d = 3.8499 | 23.083 |
| d = 2.3399 | 38.440 |

Example 19

Production Method of Benzenesulfonate of Compound A (β Crystal)

To compound A (507 mg) was added tetrahydrofuran (5.0 mL) and stirred at room temperature. After confirming dissolution, benzenesulfonic acid monohydrate (202 mg) was added at the same temperature, and stirred for another 1.5 hours. The precipitated solid was collected by filtration, and dried under reduced pressure, to obtain benzenesulfonate of compound A in white (591 mg).

¹H-NMR (500 MHz, DMSO-$d_6$):

δ 4.05 (s,2H), 4.47 (s,2H), 7.27-7.38 (m,7H), 7.58-7.60 (m,2H), 7.80 (d,J=9.2 Hz,2H), 8.02 (dd,J=7.6,1.8 Hz,1H), 8.16 (s,1H), 8.24 (d,J=5.5 Hz,1H), 8.59 (dd,J=4.9,1.5 Hz,1H), 10.05 (bs,1H), 10.66 (s,1H)

PXRD:

TABLE 14

| Peak Angstrom | Angle 2θ° |
| --- | --- |
| d = 8.0767 | 10.945 |
| d = 6.8137 | 12.982 |
| d = 4.2876 | 20.699 |
| d = 4.1260 | 21.519 |
| d = 3.9623 | 22.420 |

TGA:

Endothermic peak: 205.5° C.

In the analysis of PXRD in the foregoing [Production examples], copper radiation (40 kV/40 mA) was used as a radiation source, and measurement was conducted with the following scanning parameters: scan axis: 2θ/θ, range: 2.500-40.000°, scanning mode: continuous, sampling width: 0.020°, and scan speed: 4.000°/min.

As to the TGA analysis, about 5 mg of a sample was used, and each sample was scanned at 25.0 to 300.0° C. at a rate of 10.00° C/minute. At this time, a nitrogen gas was made to constantly flow in a crucible at a flow rate of 150.0 mL/minute.

<Storage Stability Tests for Benzenesulfonate, Methanesulfonate and P-Toluenesulfonate of Compound A (1-week Preliminary Stability Test)>

(Test Method)

For benzenesulfonate, methanesulfonate and p-toluenesulfonate of compound A, after storing under the conditions of 40° C. 75% RH, 60° C. or light (1000 lux/hr), the content of each salt of compound A was measured by HPLC. The percentage of change, relative to the content before storage of 100%, was calculated.

(Test Result)

TABLE 15

| Storage condition | Benzene-sulfonate | Methane-sulfonate | p-toluene-sulfonate |
| --- | --- | --- | --- |
| 40° C. 75% RH/1 week | 100.0% | 99.8% | 92.3% |
| 60° C./1 week | 100.0% | 99.9% | 99.3% |
| 1000 lux/hr, 1 week | 100.0% | 99.1% | 99.8% |

<Side Effect Verification Test (Rat 1-week Repeated Oral Administration Toxicity Test of Compound A (free body) and Rat 4-week Repeated Oral Administration Toxicity Test of Benzenesulfonate of Compound A)>

1) Rat 1-week repeated oral administration toxicity test of compound A (free body)

(Test and Observation Method)

i) To Crl:CD (SD) rat was orally administered compound A (10 mL/kg (body weight), 30 mL/kg (body weight)) suspended in a 1% methylcellulose liquid once a day for 7 days.

ii) After completion of the administration, the rat was exsanguinated to death under ether anesthesia, then the stomach was removed, fixed in a 10% neutral buffered formalin aqueous solution, and then stained with hematoxylin-eosin to prepare a specimen, and the change in the stomach was observed histopathologically.

2) Rat 4-week repeated oral administration toxicity test of benzenesulfonate of compound A (Test and Observation Method)

i) To Crl:CD (SD) rat was orally administered benzenesulfonate of compound A (10 mL/kg (body weight), 30 mL/kg (body weight)) suspended in a 1% methylcellulose liquid once a day for 4 weeks.

ii) After completion of the administration, the rat was exsanguinated to death under ether anesthesia, then the stomach was removed, fixed in a 10% neutral buffered formalin aqueous solution, and then stained with hematoxylin-eosin to prepare a specimen, and the change in the stomach was observed histopathologically.

(Test Result)

In contrast to compound A for which mineral deposition in the stomach was observed after 1-week repeated oral administration, mineral deposition in the stomach was not observed even after 4-week repeated oral administration for benzenesulfonate of compound A.

Formulation Examples

Representative formulation examples of the present compound will be shown below.

Prescription Example 1

Tablet (in 100 mg)

| | |
|---|---|
| Present compound | 1 mg |
| Lactose | 66.4 mg |
| Corn starch | 20 mg |
| Carboxymethyl cellulose calcium | 6 mg |
| Hydroxypropyl cellulose | 4 mg |
| Magnesium stearate | 0.6 mg |

By appropriately varying the kind and/or the amount of the present compound and/or the additives, a desired tablet can be obtained. Such a tablet can be coated with a coating agent (for example, normal coating agents such as hypromellose, macrogol and silicone resin) to obtain an intended coated tablet.

Prescription Example 2

Capsule (in 150 mg)

| | |
|---|---|
| Present compound | 5 mg |
| Lactose | 145 mg |

By appropriately varying the mixing ratio of the present compound and lactose, a desired capsule can be obtained.

Prescription Example 3

Eye Drop (in 100 mL)

| | |
|---|---|
| Present compound | 100 mg |
| Sodium chloride | 900 mg |
| Polysorbate 80 | 200 mg |
| Benzalkonium chloride | 5 mg |
| Sodium hydroxide | quantum libet |
| Hydrochloric acid | quantum libet |
| Sterilized purified water | quantum libet |

By appropriately varying the kind and/or the amount of the present compound and/or the additives, a desired eye drop can be obtained.

INDUSTRIAL APPLICABILITY

The present invention provides benzenesulfonate of compound A that is highly safe, excellent in storage stability, and useful as a pharmaceutical, a crystal of the same, a crystal polymorph thereof, and production methods thereof The present invention also provides a pharmaceutical containing at least one selected from the group consisting of benzenesulfonate of compound A, a crystal of the same, and a crystal polymorph thereof

The invention claimed is:

1. A crystal of benzenesulfonate of 2-[[[2-[(hydroxyacetyl) amino]-4-pyridinyl]methyl]thio]-N-[4-(trifluoromethoxy) phenyl]-3-pyridiriecarboxamide having characteristic peaks at 4.4 angstroms, 3,8 angstroms and 2,3 angstroms as a d value of powder X-ray diffraction pattern.

2. A crystal of benzenesulfonate of 2-[[[2-((hydroxyacetyl) amino]-4-pyridinyl]methyl]thio]-N[4-(trifluoromethoxy) phenyl]-3-pyridinecarboxamide having characteristic peaks at 8.1 angstroms, 6.8 angstroms, 4.1 angstroms and 4.0 angstroms as a d value of powder X-ray diffraction pattern.

* * * * *